US008658158B2

(12) United States Patent
Coffey et al.

(10) Patent No.: US 8,658,158 B2
(45) Date of Patent: *Feb. 25, 2014

(54) SENSITIZATION OF CHEMOTHERAPEUTIC AGENT RESISTANT NEOPLASTIC CELLS WITH A VIRUS

(71) Applicants: Matthew C. Coffey, Calgary (CA); Bradley G. Thompson, Calgary (CA)

(72) Inventors: Matthew C. Coffey, Calgary (CA); Bradley G. Thompson, Calgary (CA)

(73) Assignee: Oncolytics Biotech Inc., Calgary, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/625,259

(22) Filed: Sep. 24, 2012

(65) Prior Publication Data
US 2013/0017172 A1 Jan. 17, 2013

Related U.S. Application Data

(63) Continuation of application No. 13/109,631, filed on May 17, 2011, now abandoned, which is a continuation of application No. 12/555,453, filed on Sep. 8, 2009, now Pat. No. 7,964,187, which is a continuation of application No. 11/809,293, filed on May 31, 2007, now Pat. No. 7,608,257, which is a continuation of application No. 10/076,074, filed on Feb. 15, 2002, now Pat. No. 7,264,798.

(60) Provisional application No. 60/270,363, filed on Feb. 20, 2001.

(51) Int. Cl.
A61K 39/15 (2006.01)
C12N 15/63 (2006.01)

(52) U.S. Cl.
USPC ..... 424/93.6; 424/93.1; 424/93.3; 424/215.1; 435/320.1

(58) Field of Classification Search
None
See application file for complete search history.

(56) References Cited

U.S. PATENT DOCUMENTS

| 6,100,243 | A | 8/2000 | Frisch |
| 6,136,307 | A | 10/2000 | Lee et al. |
| 6,428,968 | B1 | 8/2002 | Molnar-Kimber et al. |
| 6,565,831 | B1 | 5/2003 | Coffey et al. |
| 7,163,678 | B2 * | 1/2007 | Norman et al. |
| 7,264,798 | B2 | 9/2007 | Coffey et al. |
| 7,608,257 | B2 | 10/2009 | Coffey et al. |
| 7,799,329 | B2 | 9/2010 | Coffey et al. |
| 7,964,186 | B2 | 6/2011 | Coffey et al. |
| 7,964,187 | B2 | 6/2011 | Coffey et al. |
| 8,066,985 | B2 * | 11/2011 | Lee et al. ............ 424/93.21 |
| 8,071,087 | B2 * | 12/2011 | Lee et al. ............ 424/93.3 |

FOREIGN PATENT DOCUMENTS

| CA | 2283280 A1 | 2/1999 |
| CA | 2360833 A1 | 8/2000 |
| WO | WO9418992 A1 | 9/1994 |
| WO | WO94025627 A1 | 11/1994 |
| WO | WO9607322 A1 | 3/1996 |
| WO | WO9918799 A1 | 4/1999 |
| WO | WO0050051 A2 | 8/2000 |

OTHER PUBLICATIONS

Steele et al. Cancer Therapy, 1995, vol. 10 (4), pp. 307-315.*
Andreansky et al., The application of genetically engineered herpes simplex viruses to the treatment of experimental brain turmors, Proc. Natl. Acad. Sci., 93(21):11313-11318 (1996).
Baldari et al., Interluekin-2 promoter activation in T-cells expressing activated Ha-ras, J. Biol. Chem., 267 (7):4289-4291 (1992).
Bar-Eli et al., Perferential cytotoxic effect of Newcastle disease virus on lymphoma cells, J. Cancer Res. Clin. Oncol., 122:409-415 (1996).
Bergmann et al., A Genetically Engineered Influenza A Virus with ras-Dependent Oncolytic Properties, Cancer Res. 61:8188-8193 (2001).
Bischoff Jr. et al., An Advenovirus Mutant that Replicates Selectively in p53-Deficient Human Tumor Cells, Science, 274(5286):373-6 (1996).
Blagoslelonny et al., In vitro Evaluation of ap53-Expressing Adenovirus as an Anti-Cancer Drug, Int. J. Cancer, 67(3):386-392 (1996).
Bona et al., Chapter II in Textbook of Immunology, edited by Bone et al., Hardwood Academic Publishers, pp. 331-334 (1996).
Borst et al., A Family of Drug Transporters: the Multidrug Resistance Associated Proteins, j. Nat. Cancer Inst., 92(16):1295-1302 (2000).
Bryson et al., Characteristics of reovirus-mediated chemoimmunotherapy of murine LI210 leukemia, Cancer Immunol. Immunother., 26:I32-I38 (1988).
Chandran et al., Protease Cleavage of Reovirus Capsid Protein ILIIILIC is Blocked by Alkyl Sulfate Detergents, Yielding a New Type of Infectious Subvirion Particle, J. of Virology, 72(1):467-75 (1998).
Chang et al., Rescue of Vaccinia Virus Lacking the E3L Gene by Mutants of E3L, J. Virol., 69:6605-6608 (1995).

(Continued)

*Primary Examiner* — Bao Li
(74) *Attorney, Agent, or Firm* — Kilpatrick, Townsend & Stockton LLP

(57) ABSTRACT

The present invention relates to a method of increasing the sensitivity of neoplastic cells to chemotherapeutic agents by using a virus, a method of treating proliferative disorders with a virus and chemotherapeutic agents, and a method for preventing a neoplasm from developing drug resistance to chemotherapeutic agents. The virus is preferably a reovirus.

19 Claims, 1 Drawing Sheet

(56) References Cited

OTHER PUBLICATIONS

Chang et al., The E3L gene of vaccinia virus encodes an inhibitor of the interferon-induced, doublestranded RNA-dependent protein kinase, Proc. Natl. Acad. Sci., 89:4825-4829 (1992).
Chang et al., Identification of a Conserved Motif that is Necessary for Binding of the Vaccinia Virus E3L Gene Products to Double-Stranded RNA, Virol., 194:537-547 (1993).
Clarke et al., Reovirus-induced apoptosis is mediated by TRAIL, Journal of Virology, 74(17):8135-8139 (2000).
Coffey et al., Reovirus Therapy of Tumors with Activated Ras Pathway, Science, 282:1332-1334 (1998).
DeVita, The Relationship Between Tumor Mass and Resistance to Chemotherapy. Implications for Surgical Adjuvant Treatment of Cancer, Cancer, 51:1209-1220 (1983).
Duncan et al., Conformational and Functional Analysis of the C-Terminal Globular Head of the Reovirus Cell Attachment Protein, Virology, 182(2):810-9 (1991).
Farassati et al., Oncogenes in Ras signalling pathway dictate host-cell permissiveness to herpes simplex virus 1, Nat. Cell Biol., 3(8):745-750 (2001).
Fuertes et al., Current Medicine Chemistry, 10:257-66 (2003).
Fueyo et al., A Mutant Oncolytic Adenovirus Targeting the Rb Pathway Produces Anti-Glioma Effect in Vivo, Oncogene, 19(1):2-12 (2000).
Fujiwara et al., Induction of chemotherapy in human lung cancer cells in vivo by Adenoviruemediated transfer of the wild-type p53 gene, Cancer Research, 54:2287-2291 (1994).
Fujiwara et al., Induction of Chemosensitivty in Human Lung Cancer Cells in Vivo by Adenovirus-mediated Transfer of the Wild-Type p53 Gene, Cancer Research, 54:2298-2291 (1994).
Grant et al., Overexpression of Multi drug Resistance-Associated Protein (MRP) Increases Resistance to Natural Product Drugs, Cancer Res., 54:357-361 (1994).
Heise et al., Replication-selective adenoviruses as oncolytic agents, J. Clin. Invest., 105(7):847-51 (2000).
Heise et al., Efficacy with a Replication-selective Adenoviurs Plus Cisplatin-based Chemotherapy: Dependence on Sequencing but not p53 Functional Status or Route of Administration, Clinical Can. Res., 6:4909-4914 (2000).
Hirasawa et al., Reovirus therapy of metastatic cancer models in immune-competent mice on the website of Oncolytics Biotech Inc. (http://www.oncolyticsbiotech.com/02280p1.html) (2001).
Hirasawa et al., Systemic Reovirus Therapy of Metastatic Cancer Models in Immune-competent Mice, Cancer Res., 63(2):348-53 (2003).
Kawagishi-Kobayashi et al., Regulation of the Protein Kinase PKR by the Vaccinia Virus Pseudosubstrate Inhibitor K3L is Dependent on Residues Conserved between the K3L Protein and the PKR Substrate eIF2α, Mol. Cell. Biol., 17:4146-4158 (1997).
Kim, Replication-selective oncolytic adenoviruses: virotherapy aimed at genetic targets in cancer, Oncogene, 19:6660-6669 (2000).
Khuri et al., A controlled trial of intratumoral ONYX-015, a selectively replicating adenovirus, in combination with cisplatin and 5-fluorouracil in patients with recurrent head and neck cancer, Nat. Med., 6(8):862-3 (2000).
Liu, Oncogene expression in adriamycin and platinum resistant cell lines, Zhonghua Yi Zue Za Zhi, 73(9):552-4, 576 (1993).
Mah et al., The N-Terminal Quarter of Reovirus Cell Attachment Protein 0-1 Possesses Intrinsic Virion-Anchoring Function, Virology, 179(1):95-103 (1990).
Mercer University, Mercer University Homepage, pp. 1-2 (1996).
Nemunaitis, Oncolytic Viruses, Invest. New Drugs, 17:375-386 (1999).
Orr et al., Oncogene, 22:7280-95 (2003).
Pastan et al., Multidrug Resistance, Annu. Rev. Med., 42:277-286 (1991).
Prigent et al., Enhanced tumorigenic behavior of gliobastoma cells expressing a truncated epidermal growth factor receptor is mediated through the ras-she-grb2 pathway, Biologic. Chem., 271:25635-45 (1996).
Rayter et al., p21ras mediates control of IL-2 gene promoter function in T cell activation, EMBO Journal, 11(12):4549-4556 (1992).
Reichard et al., Newcastle Disease Virus Selectively Kills Human Turmor Cells, J. of Surgical Research, 52:448-453 (1992).
Romano et al., Inhibition of Double-Stranded RNA-Dependent Protein Kinase PKR by Vaccinia Virus E3: Role of Complex Formation and the E3 N-Terminal Domain, Mol. Cell. Biol., 18(12):7304-7316 (1998).
Sansing et al., Evaluation of time and dose in treating mammary adenocarcinoma with immunostimulants, Cancer Immunology Immunotherapy, 2(1):63-68 (1977).
Sharp et al., The Vaccinia Virus E3L Gene Product Interacts with both the Regulatory and the Substrate Binding Regions of PKR: Implications for PKR Autoregulation, Virology, 250:302-315 (1998).
Smith et al., Polypeptide Components of Virions, Top Component and Cores of Reovirus Type 3, Virology, 39:791-800 (1969).
Smith et al., Oncolytic viruses as novel anticancer agents: turning one scourge against another, Exp. Opin. Invest. Drugs, 9:311-27 (2000).
Steele et al., Reovirus type 3 chemoimmunotherapy of murine lymphoma is abrogated by cyclosporin Cancer Biotherapy, 10(4):307-315 (1995).
Stojdl et al., Exploiting tumor-specific defects in the interferon pathway with a previously unknown oncolytic virus, Nat. Med., 6(7):821-825 (2000).
Strong et al., The molecular basis of viral oncolysis: usurpation of the Ras signaling pathway by reovirus, EMBO J., 17:3351-3361 (1998).
Turner et al., Site-Directed Mutagenesis of the C-terminal Portion of Reovirus Protein a1: Evidence for a Conformation-Dependent Receptor Binding Domain, Virology, 186(1):219-27 (1992).
Umezawa et al., Isolation of a new vinca alkaloid from the leaves of *Ervantimia microphylla* as an inhibitor of ras functions, Anticancer Research, 14:2413-2418 (1994).
Umezawa et al., Growth inhibition of K-ras-expressing tumours by a new vinca alkaloid, conophylline, in nude mice, Drugs Exptl. Clin. Res., 22(2):36-40 (1996).
Ueno et al., E1A-mediated paclitaxel sensitization in HER-2/neu-overexpressing ovarian cancer SKOV3.ip1 through apoptosis involving the caspase-3 pathway, Clinical Cancer Research, 6(1):250-259 (2000).
William et al., Cancer Immunol. Immunother., 23(2):87-92 (1986).
Yoon et al., An oncolytic herpes simplex virus type I selectively destroys diffuse liver metastases from colon carcinoma, FASEB, J., 14: 301-311 (2000).
Zhang et al., Anti-tumorigenic effect of a K-ras ribozyme against human lung cancer cell line heterotransplants in nude mice, Gene Ther., 7: 2044-2050 (2000).
Zorn et al., Induction of Cytokines and Cytotoxicity against Tumor Cells by Newcastle Disease Virus, Cancer Biotherapy, 9(3):225-235 (1994).

\* cited by examiner

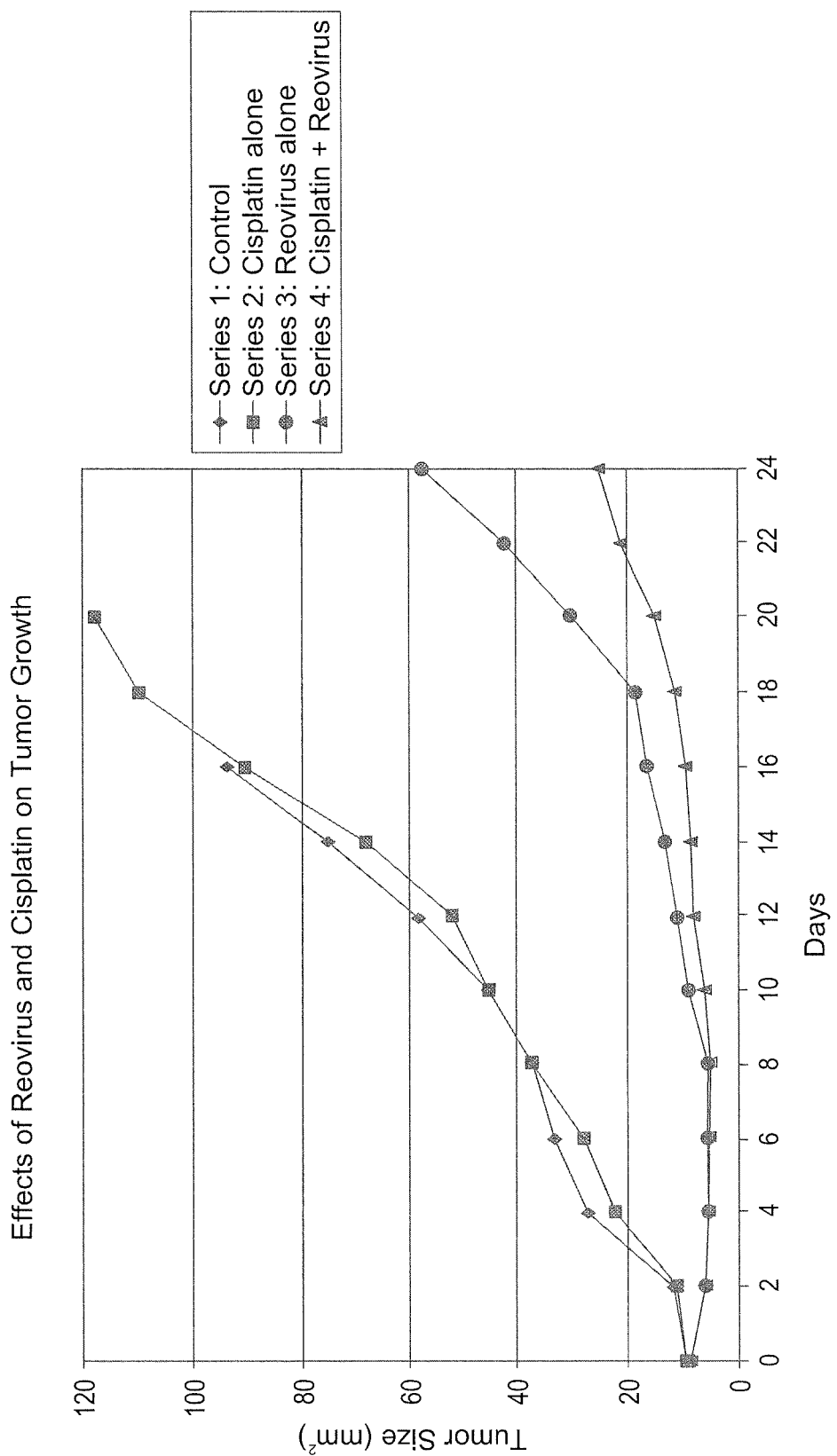

SENSITIZATION OF CHEMOTHERAPEUTIC AGENT RESISTANT NEOPLASTIC CELLS WITH A VIRUS

RELATED APPLICATION

This application is a continuation application of U.S. patent application Ser. No. 13/109,631, filed May 17, 2011, which is currently pending and which is a continuation of U.S. patent application Ser. No. 12/555,453, filed Sep. 8, 2009, now U.S. Pat. No. 7,964,187, which is a continuation application of U.S. patent application Ser. No. 11/809,293, filed May 31, 2007, now U.S. Pat. No. 7,608,257, which is a continuation application of U.S. patent application Ser. No. 10/076,074, filed Feb. 15, 2002, now U.S. Pat. No. 7,264,798, which claims the benefit of U.S. Provisional Application Ser. No. 60/270,363, filed Feb. 20, 2001. These applications are, hereby incorporated by reference in their entireties.

FIELD OF THE INVENTION

The present invention relates to a method of increasing the sensitivity of neoplastic cells to chemotherapeutic agents by using a virus, and a method of treating proliferative disorders with a virus and chemotherapeutic agents. In particular, the virus is a reovirus.

REFERENCES

U.S. Pat. No. 6,136,307.
WO 94/18992, published Sep. 1, 1994.
WO 94/25627, published Nov. 10, 1994.
WO 99/18799, published Apr. 22, 1999.
Andreansky, S. A., et al., "The application of genetically engineered herpes simplex viruses to the treatment of experimental brain tumors", *Proc. Natl. Acad. Sci.* 93(21): 11313-11318 (1996).
Bar-Eli, N., et al., "preferential cytotoxic effect of Newcastle disease virus on lymphoma cells", *J. Cancer Res. Clin. Oncol.* 122: 409-415 (1996).
Bergmann, M., et al., "A genetically engineered influenza A virus with ras-dependent oncolytic properties", *Cancer Res.* 61:8188-8193 (2001).
Bischoff J R. et al., "An Adenovirus Mutant that Replicates Selectively in p53-Deficient Human Tumor", *Science* 274 (5286):373-6 (1996).
Blagoslelonny, M. V., et al., "in vitro Evaluation of a p53-Expressing Adenovirus as an Anti-Cancer Drug", *Int. J. Cancer* 67(3):386-392 (1996).
Borst et al., "A family of drug transporters: the multidrug resistance-associated proteins", *J. Natl. Cancer Inst.* 92(16): 1295-1302 (2000).
Chandron and Nibert, "Protease cleavage of reovirus capsid protein mu1 and mu1C is blocked by alkyl sulfate detergents, yielding a new type of infectious subvirion particle", *J. of Virology* 72(1):467-75 (1998).
Chang et al., *J. Virol.* 69:6605-6608 (1995).
Chang et al., *Proc. Natl. Acad. Sci.* 89:4825-4829 (1992).
Chang et al., *Virol.* 194:537-547 (1993).
Coffey, M. C., et al., "Reovirus therapy of tumors with activated Ras pathway", *Science* 282: 1332-1334 (1998).
DeVita, Jr., "The relationship between tumor mass and resistance to chemotherapy. Implications for surgical adjuvant treatment of cancer", *Cancer* 51:1209-1220 (1983).
Duncan et al., "Conformational and functional analysis of the C-terminal globular head of the reovirus cell attachment protein", *Virology* 182(2):810-9 (1991).
Farassati, F., et al., "Oncogenes in Ras signalling pathway dictate host-cell permissiveness to herpes simplex virus 1", *Nat. Cell Biol.* 3(8):745-750 (2001).
Fields, B. N. et al., *Fundamental Virology.* 3rd Edition, Lippincott-Raven (1996).
Fueyo, 3., et al., "A Mutant Oncolytic Adenovirus Targeting the Rb Pathway Produces Anti-Glioma Effect in Vivo", *Oncogene* 19(1):2-12 (2000).
Grant et al., "Overexpression of multidrug resistance-associated protein (MRP) increases resistance to natural product drugs", *Cancer Res.* 54: 357-361 (1994).
Heise, C. et al., "Replication-selective adenoviruses as oncolytic agents", *J. Clin. Invest.* 105(7):847-51 (2000).
Kawagishi-Kobayashi, M. et al., *Mol. Cell. Biol.* 17:4146-4158 (1997).
Mah et al., "The N-terminal quarter of reovirus cell attachment protein sigma 1 possesses intrinsic virion-anchoring function", *Virology* 179(1):95-103 (1990).
Nemunaitis, J., *Invest. New Drugs* 17:375-386 (1999).
Pastan and Gottesman, "Multidrug resistance", *Annu. Rev. Med.* 42: 277-286 (1991).
Reichard, K. W., et al., "Newcastle Disease Virus Selectively Kills Human Tumor Cells", *J. of Surgical Research* 52:448-453 (1992).
Romano et al., *Mol. Cell. Bio.* 18(12):7304-7316 (1998).
Sharp et al., *Virology* 250:302-315 (1998).
Smith, R E., et al., "Polypeptide components of virions, top component and cores of reovirus type 3", *Virology,* 39:791-800 (1969).
Stojdl, D. F., et al., "Exploiting Tumor-Specific Defects in the Interferon Pathway with a Previously Unknown Oncolytic Virus", *Nat. Med.* 6(7):821-825 (2000).
Strong, J. E., et al., "The molecular basis of viral oncolysis: usurpation of the Ras signaling pathway by reovirus", *EMBO J.* 17: 3351-3362 (1998).
Turner and Duncan, "Site directed mutagenesis of the C-terminal portion of reovirus protein sigmal: evidence for a conformation-dependent receptor binding domain", *Virology* 186(1):219-27 (1992).
Yoon, S. S., et al., "An Oncolytic Herpes Simplex Virus Type I Selectively Destroys Diffuse Liver Metastases from Colon Carcinoma", *FASEB J.* 14:301-311 (2000).
Zorn, U. et al., "Induction of Cytokines and Cytotoxicity against Tumor Cells by Newcastle Disease Virus", *Cancer Biotherapy* 9(3):22-235 (1994).

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Cancer is one of the leading causes of death. Although it has been the focus of medical research for a long period of time, the main cancer therapies to date remain to be surgery, radiation therapy and chemotherapy. Each one of these therapies is subject to limitations which are not currently overcome, and the search for an improved therapy continues.

One significant problem of chemotherapy is that tumors can develop resistance to drugs. For example, a drug may be highly effective when it is first introduced to the patient, killing tumor cells and reducing the size of the tumor such that the patient goes into a remission. However, the tumor may regrow after a period of time, and this time the same drug is not effective at all at killing the regrown tumor cells. This phenomenon of progressive drug resistance is believed to be due to a small population of drug resistant cells in the tumor which survives the initial drug treatment while the majority of the tumor is killed. These resistant cells eventually grow back to form a tumor comprising essentially only drug resistant cells.

Treatment at the outset with a combination of drugs was proposed as a solution, given the small probability that mutations which lead to two or more different drug resistance pathways would arise spontaneously in the same cell (DeVita, Jr., 1983). However, it has been discovered that cells which are resistant to one drug are often resistant to multiple drugs, including structurally unrelated drugs which are capable of killing tumor cells by different pathways. Therefore, combination drug therapy does not solve the problem.

Although the mechanisms are not completely clear, the best documented and clinically relevant mechanism for multidrug resistance in tumor cells is correlated with the expression of P-glycoprotein, the product of the MDR1 gene. P-glycoprotein is a broad specificity efflux pump located in the cell membrane, and functions by decreasing the intracellular accumulation of many lipophilic cytotoxic drugs, including some widely used anticancer agents such as anthracyclines, vinca alkaloids, epipodophyllotoxins, actinomycin D and taxol, thereby rendering cells resistant to these drugs (Pastan et al., 1991).

In addition to MDR1, another pleiotropic drug transporter has then been discovered (Grant et al., 1994). This protein, termed the Multidrug Resistance-associated Protein (MRP), has been shown to confer a pattern of resistance to cytotoxic drugs, particularly chemotherapeutic drugs, similar to the P-glycoprotein transporter encoded by the MDR1 gene. Subsequently, an increasing number of MRP related proteins have been discovered (Borst et al., 2000). Each one may have a different drug specificity, but the physiologic functions are not completely known.

Therefore, the causes of drug resistance are not fully understood and there is still a need for methods to overcome drug resistance in order to treat tumors more effectively.

SUMMARY OF THE INVENTION

The present invention provides a method of sensitizing drug resistant cells to chemotherapeutic agents by the use of a virus, particularly a reovirus. Reovirus has recently been discovered as a selective anticancer agent which kills ras-activated neoplastic cells but not normal cells, due to selective replication of reovirus in cells with an activated ras pathway (U.S. Pat. No. 6,136,307; Coffey et al., 1998; Strong et al., 1998). Unexpectedly, it was further discovered in the present invention that reovirus increased the sensitivity of cells to chemotherapeutic agents as well. Thus, a tumor which is refractory to cisplatin was treated with a combination of cisplatin and reovirus, and the results indicate that the combination was more effective than reovirus alone. Since cisplatin had no effect on the tumor when administered in the absence of reovirus, the effect of the combination was not simply an additive or synergistic result of the individual effects. Instead, reovirus sensitized the tumor to a chemotherapeutic agent to which the tumor is normally refractory.

Accordingly, one aspect of the present invention provides a method of sensitizing a neoplastic cell, comprising
  (a) administering to said cell an effective amount of reovirus; and
  (b) administering an effective amount of the chemotherapeutic agent to said cell.

The cell is preferably a ras-activated neoplastic cell. Most preferably, the reovirus is administered under conditions which result in infection of the neoplastic cell by the reovirus. The cell may be susceptible to the chemotherapeutic agent in the absence of reovirus, but it is preferably refractory to the chemotherapeutic agent.

To sensitize the cell, reovirus can preferably be administered prior to administration of the chemotherapeutic agent. Alternatively, in another preferred embodiment, reovirus and the chemotherapeutic agent can be administered concurrently with each other. Both the reovirus and chemotherapeutic agent may individually be administered in a single dose or multiple doses.

The neoplastic cell is preferably located in a mammal, particularly a dog, cat, sheep, goat, cattle, horse, pig, human or non-human primates. The cell is most preferably located in a human.

The present invention may be used to sensitize cells to any chemotherapeutic agent. Preferred chemotherapeutic agents include 5-fluorouracil, mitomycin C, methotrexate, hydroxyurea, cyclophosphamide, dacarbazine, mitoxantrone, anthracyclins (e.g. epirubicin and doxorubicin), carboplatin, cisplatin, taxol, taxotere, tamoxifen, anti-estrogens, and interferons. More preferably, the chemotherapeutic agent is a platinate or taxol. The most preferred chemotherapeutic agent is cisplatin.

The reovirus may be any reovirus, including mammalian and avian reovirus. Preferably, the reovirus is a mammalian virus, particularly a human reovirus. The human reovirus is preferably a serotype 3 reovirus and most preferably a Dearing strain serotype 3 reovirus.

Also provided by the present invention is a method of treating a subject with a proliferative disorder, said subject comprising neoplastic cells which are refractory to a chemotherapeutic agent, comprising:
  (a) administering to the subject an effective amount of reovirus under conditions which result in infection of the neoplastic cells by the reovirus; and
  (b) administering an effective amount of the chemotherapeutic agent to said subject.

The reovirus may be administered any time with respect to the chemotherapeutic agent. Preferably, the reovirus is administered prior to or concurrently with administration of the chemotherapeutic agent. Preferably the reovirus is administered in multiple doses. The chemotherapeutic agent may also be administered in multiple doses. It is contemplated that the reovirus may be administered in multiple doses prior to any administration of the chemotherapeutic agent.

The subject is preferably a mammal, particularly a dog, cat, sheep, goat, cattle, horse, pig, human or non-human primates, and most preferably a human.

The proliferative disorder may be solid tumor, particularly lung cancer, prostate cancer, colorectal cancer, thyroid cancer, renal cancer, adrenal cancer, liver cancer, pancreatic cancer, breast cancer and central and peripheral nervous system cancer. To treat the solid tumor, reovirus may be administered, for example, by injection into or near the solid tumor or by systematic administration.

The proliferative disorder may alternatively be a hematopoietic tumor, particularly lymphomas and leukemias.

The proliferative disorder may be an original tumor or a metastatic tumor.

Also provided is a method for preventing a neoplasm in a subject from developing drug resistance to a chemotherapeutic agent, comprising:

(a) administering to the subject an effective amount of reovirus under conditions which result in infection of the neoplasm by the reovirus; and (b) administering to the subject an effective amount of a chemotherapeutic agent.

The reovirus may be administered any time with respect to the chemotherapeutic agent. Preferably, the reovirus is administered prior to or concurrently with administration of the chemotherapeutic agent. Preferably the reovirus is administered in multiple doses. The chemotherapeutic agent may also be administered in multiple doses. It is contemplated that the reovirus may be administered in multiple doses prior to any administration of the chemotherapeutic agent.

The subject is preferably a mammal, particularly a dog, cat, sheep, goat, cattle, horse, pig, human or non-human primates, and most preferably a human.

Preferably, administration of the reovirus prevents the neoplasm from developing drug resistance to multiple drugs, including structurally unrelated drugs. Accordingly, a preferred embodiment of the present invention provides a method for preventing a neoplasm in a subject from developing drug resistance to a chemotherapeutic agent wherein drug resistance to a second chemotherapeutic agent is also prevented, which method comprising:

(a) administering to the subject an effective amount of reovirus under conditions which result in infection of the neoplasm by the reovirus; and (b) administering to the subject an effective amount of a chemotherapeutic agent.

Other aspects of the present invention provide method of sensitizing neoplastic cells, treating proliferative disorder, or preventing development of drug resistance using other viruses in the same manner as reovirus. The virus useful in the present invention is preferably capable of selectively infecting neoplastic cells. Preferably, the virus is selected from the group consisting of modified adenovirus, modified HSV, modified vaccinia virus, modified parapoxvirus orf virus, delNS1 virus, p53-expressing viruses, the ONYX-015 virus, the Delta24 virus, vesicular stomatitis virus, the herpes simplex virus 1 mutant which is defective in hrR3, Newcastle disease virus, encephalitis virus, herpes zoster virus, hepatitis virus, influenza virus, varicella virus, and measles virus. More preferably, the virus is selected from the group consisting of modified adenovirus, modified HSV, modified vaccinia virus, modified parapoxvirus orf virus, delNS1 virus, p53-expressing viruses, the ONYX-015 virus, the Delta24 virus, and vesicular stomatitis virus.

BRIEF DESCRIPTION OF THE DRAWINGS

FIG. 1 shows the effects of reovirus and cisplatin on tumor growth. Animals bearing syngeneic tumors were given mock treatment (Series 1), cisplatin alone (Series 2), reovirus alone (Series 3) or the combination of cisplatin and reovirus (Series 4). The results indicate that the tumors were refractory to cisplatin. However, in the presence of reovirus, the tumors became sensitive to cisplatin.

DETAILED DESCRIPTION OF THE INVENTION

The present invention is directed to a method of sensitizing drug resistant cells to chemotherapeutic agents by the use of a virus, particularly a reovirus. Reovirus has recently been discovered as a selective anticancer agent which kills ras-activated neoplastic cells but not normal cells, due to selective replication of reovirus in cells with an activated ras pathway (U.S. Pat. No. 6,136,307; Coffey et al., 1998; Strong et al., 1998). Unexpectedly, it was further discovered in the present invention that reovirus increased the sensitivity of cells to chemotherapeutic agents as well. The present invention thus provides a method of enhancing both the efficacy and selectivity of cancer chemotherapy. It may also be used to prevent the development of progressive drug resistance.

Prior to describing the invention in further detail, the terms used in this application are defined as follows unless otherwise indicated.

Definitions

"Sensitizing" a neoplastic cell to a chemotherapeutic agent, as used herein, refers to the act of enhancing the sensitivity of a neoplastic cell to a chemotherapeutic agent.

"Sensitivity" of a neoplastic cell to a chemotherapeutic agent is the susceptibility of the neoplastic cell to the inhibitory effect of the chemotherapeutic agent. For example, sensitivity of a neoplastic cell to a chemotherapeutic agent is indicated by reduction in growth rate of the cell in response to the chemotherapeutic agent. The sensitivity may also be demonstrated by a reduction of the symptoms caused by the neoplastic cells.

A neoplastic cell that is "refractory" to a chemotherapeutic agent is a neoplastic cell not killed or growth inhibited by the chemotherapeutic agent. To determine if a neoplastic cell is growth inhibited, the growth rate of the cell in the presence or absence of the chemotherapeutic agent can be determined by established methods in the art. The neoplastic cell is not growth inhibited by the chemotherapeutic agent if the growth rate is not significantly different with or without the chemotherapeutic agent.

A tumor that is "refractory" to a chemotherapeutic agent is a tumor of which the rate of size increase or weight increase does not change in the presence of the chemotherapeutic agent. Alternatively, if the subject bearing the tumor displays similar symptoms or indicators of the tumor whether the subject receives the chemotherapeutic agent or not, the tumor is refractory to the chemotherapeutic agent. For example, white cell count is commonly used as an indicator of leukemia. If the white cell count of a leukemia patient does not significantly change after receiving a chemotherapeutic drug, the leukemia of this patient is refractory to the chemotherapeutic drug.

A "neoplastic cell", also known as a "cell with a proliferative disorder", refers to a cell which proliferates at an abnormally high rate. A new growth comprising neoplastic cells is a neoplasm, also known as a tumor. A neoplasm is an abnormal tissue growth, generally forming a distinct mass, that grows by cellular proliferation more rapidly than normal tissue growth. A neoplasm may show partial or total lack of structural organization and functional coordination with normal tissue. As used herein, a neoplasm is intended to encompass hematopoietic tumors as well as solid tumors.

A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

A "proliferative disorder" is a disease or condition caused by cells which grow more quickly than normal cells, i.e., neoplastic cells. Proliferative disorders include benign tumors and malignant tumors. When classified by structure of the tumor, proliferative disorders include solid tumors and hematopoietic tumors.

"Ras-activated neoplastic cells" or "ras-mediated neoplastic cells" refer to cells which proliferate at an abnormally high rate due to, at least in part, activation of the ras pathway. The ras pathway may be activated by way of ras gene structural mutation, elevated level of ras gene expression, elevated stability of the ras gene message, or any mutation or other mechanism which leads to the activation of ras or a factor or factors downstream or upstream from ras in the ras pathway, thereby increasing the ras pathway activity. For example, activation of EGF receptor, PDGF receptor or sos results in activation of the ras pathway. Ras-mediated neoplastic cells include, but are not limited to, ras-mediated cancer cells, which are cells proliferating in a malignant manner due to activation of the ras pathway.

"Infection by reovirus" refers to the entry and replication of reovirus in a cell. Similarly, "infection of a neoplasm by reovirus" refers to the entry and replication of reovirus in the cells of a neoplasm.

A "chemotherapeutic agent" or "chemotherapeutic drug" is any chemical compound used in the treatment of a proliferative disorder. Examples of chemotherapeutic agents include, without being limited to, the following classes of agents:

nitrogen mustards, e.g. cyclophosphamide, trofosfamide, ifosfamide and chlorambucil;
nitroso ureas, e.g. carmustine (BCNU), lomustine (CCNU), semustine (methyl CCNU) and nimustine (ACNU);
ethylene imines and methyl-melamines, e.g. thiotepa;
folic acid analogs, e.g. methotrexate;
pyrimidine analogs, e.g. 5-fluorouracil and cytarabine;
purine analogs, e.g. mercaptopurine and azathioprine;
vinca alkaloids, e.g. vinblastine, vincristine and vindesine;
epipodophyllotoxins, e.g. etoposide and teniposide;
antibiotics, e.g. dactinomycin, daunorubicin, doxorubicin, epirubicin, bleomycin a2, mitomycin c and mitoxantrone;
estrogens, e.g. eiethyl stilbestrol;
gonadotropin-releasing hormone analogs, e.g. leuprolide, buserelin and goserelin;
antiestrogens, e.g. tamoxifen and aminoglutethimide;
androgens, e.g. testolactone and drostanolonproprionate;
platinates, e.g. cisplatin and carboplatin; and
interferons, including interferon-alpha, beta and gamma.

The chemotherapeutic agents of the present invention are preferably small chemical compounds. Thus, the chemotherapeutic agent has a molecular weight of preferably less than about 5,000, more preferably less than about 3,000, still more preferably less than about 2,000, and most preferably less than about 1,000.

A "platinate" is a chemotherapeutic drug that contains platinum as a central atom. Examples of platinates include cisplatin, carboplatin, oxaliplatin, ormaplatin, iproplatin, enloplatin, nedaplatin, ZD0473 (cis-amminedichloro(2-methylpyridine)-platinum (II)), BBR3464 and the like.

"Reovirus" refers to any virus classified in the reovirus genus, whether naturally occurring, modified or recombinant. Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998). For example, the virion may be treated with chymotrypsin in the presence of micelle forming concentrations of alkyl sulfate detergents to generate a new infectious subvirion particle.

The reovirus may be a recombinant (i.e. reassorted) reovirus from two or more types of reoviruses with differing pathogenic phenotypes such that it contains different antigenic determinants, thereby reducing or preventing an immune response by a mammal previously exposed to a reovirus subtype. Such recombinant virions can be generated by co-infection of mammalian cells with different subtypes of reovirus with the resulting resorting and incorporation of different subtype coat proteins into the resulting virion capsids.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner and Duncan, 1992; Duncan et al., 1991; Mah et al., 1990).

The reovirus is preferably a reovirus modified to reduce or eliminate an immune reaction to the reovirus. Such modified reovirus are termed "immunoprotected reovirus". Such modifications could include packaging of the reovirus in a liposome, a micelle or other vehicle to mask the reovirus from the mammals immune system. Alternatively, the outer capsid of the reovirus virion particle may be removed since the proteins present in the outer capsid are the major determinant of the host humoral and cellular responses.

The term "attenuated adenovirus" or "modified adenovirus" means an adenovirus in which the gene product or products which prevents the activation of PKR is lacking, inhibited or mutated such that PKR activation is not blocked. Preferably, the VA1 RNA's are not transcribed. Such attenuated or modified adenovirus would not be able to replicate in normal cells that do not have an activated ras pathway, however, it would be able to infect and replicate in cells having an activated ras pathway.

The term "attenuated HSV" or "modified HSV" means a herpes simplex virus (HSV) in which the gene product or products that prevents the activation of PKR is lacking, inhibited or mutated such that PKR activation is not blocked. Preferably, the HSV gene $_{\gamma 1}34.5$ is not transcribed. Such attenuated or modified HSV would not be able to replicate in normal cells that do not have an activated ras pathway, however, it would be able to infect and replicate in cells having an activated ras pathway.

"Parapoxvirus orf virus" is a poxvirus. It is a virus that induces acute cutaneous lesions in different mammalian species, including humans. Parapoxvirus orf virus naturally infects sheep, goats and humans through broken or damaged skin, replicates in regenerating epidermal cells and induces pustular leasions that turn to scabs (Haig et al., 1998). The term "attenuated parapoxvirus off virus" or "modified parapoxvirus orf virus" means a parapoxvirus orf virus in which the gene product or products which prevents the activation of PKR is lacking, inhibited or mutated such that PKR activation is not blocked. Preferably, the gene OV20.0L is not transcribed. Such attenuated or modified parapoxvirus orf virus would not be able to replicate in normal cells that do not have an activated ras pathway, however, it would be able to infect and replicate in cells having an activated ras pathway.

The term "attenuated vaccinia virus" or "modified vaccinia virus" means a vaccinia virus in which the gene product or products which prevents the activation of PKR is lacking, inhibited or mutated such that PKR activation is not blocked. Preferably, the E3L gene and/or the K3L gene is not transcribed. Such attenuated or modified vaccinia virus would not be able to replicate in normal cells that do not have an activated ras pathway, however, it would be able to infect and replicate in cells having an activated ras pathway.

"Administration of reovirus" to a subject refers to the act of administering reovirus to a subject in a manner so that it contacts the target neoplastic cells. The route by which the reovirus is administered, as well as the formulation, carrier or vehicle, will depend on the location as well as the type of the target cells. A wide variety of administration routes can be employed and is discussed below in further detail.

"Treating a proliferative disorder" means alleviating or eliminating the symptoms of a proliferative disorder, or slowing down the progress of a proliferative disorder.

A "metastatic tumor" is a tumor that has metastasized from a tumor located at another place in the same animal.

An "effective amount" is an amount of a chemotherapeutic agent or reovirus which is sufficient to result in the intended effect. For a chemotherapeutic agent used to treat a disease, an efficient amount is an amount sufficient to alleviate or eliminate the symptoms of the disease, or to slow down the progress of the disease. For a reovirus to sensitize a tumor to a chemotherapeutic agent, an efficient amount is an amount sufficient to increase sensitivity of the tumor to the chemotherapeutic agent.

"Progressive drug resistance" refers to the phenomenon wherein a neoplasm is initially susceptible to a chemotherapeutic agent, but the efficacy of the agent in inhibiting neoplastic growth or reducing symptoms of the disease decreases over time.

Methods

Reovirus is an effective therapeutic agent against ras-activated neoplasia because it selectively replicates in cells with an activated ras pathway (U.S. Pat. No. 6,136,307). The ras pathway is not activated in normal cells, therefore reovirus kills neoplastic cells with high selectivity. Without being limited to a theory, it is thought that viral gene transcription in normal cells correlated with phosphorylation of a cellular protein of approximately 65 kDa, determined to be double-stranded RNA-activated protein kinase (PKR), that was not observed in ras-activated cells. Phosphorylation of PKR leads to inhibition of translation, therefore viral replication can not be completed. In ras-activated cells, however, ras or its downstream factors blocks the phosphorylation of PKR, thereby allowing viral translation and replication to go on.

In the present invention, we treated tumors with a combination of reovirus and chemotherapeutic agents. Unexpectedly, we found that reovirus was capable of sensitizing neoplastic cells to chemotherapeutic agents, whereas the chemotherapeutic agents had no effect on the cells when administered alone. As shown in FIG. 1, C3H10T1/2 derived tumors were refractory to cisplatin. These tumors grew aggressively in the presence of cisplatin at a growth rate that was essentially the same as untreated tumors. In contrast, the tumors treated with both reovirus and cisplatin almost completely stopped growing. The inhibitory effect of the combination (reovirus plus cisplatin) was much higher than reovirus alone, indicating that cisplatin contributed to the killing of tumor cells. Therefore, while the cells are refractory to cisplatin, reovirus treatment increased the sensitivity of the tumor cells to the drug.

Without being limited to a theory, we believe that reovirus sensitizes tumor cells to chemotherapeutic agents by enhancing accumulation of the agents in tumor cells, or by inducing apoptosis. Reovirus is known to inhibit protein synthesis of the host cell in favor of translation of its own proteins. Therefore, reovirus infection may inhibit the synthesis of drug transporter proteins, such as MDR1 or the MRPs, and enable drugs to accumulate in the cell. Since drug transporter proteins are responsible for transporting various drugs out of the cell, including structurally unrelated drugs, inhibiting the synthesis of such transporter proteins would lead to sensitization of the cell to a variety of drugs. Alternatively, reovirus is known to induce apoptosis of the infected cells, which may render the cells more susceptible to further stress.

The present invention thus provides a valuable method of increasing both the efficacy and selectivity of chemotherapy. Selectivity has been a major problem with chemotherapy, because chemotherapeutic agents generally inhibit the growth of both normal cells and neoplastic cells. Chemotherapeutic agents do display limited selectivity, however, since neoplastic cells grow faster than most normal cells and hence are growth inhibited to a greater extent. Nevertheless, fast growing normal cells, such as bone marrow cells, tend to be severely damaged by chemotherapeutic drugs, leading to significant side effects. In contrast, reovirus is highly selective for neoplastic cells and sensitizes neoplastic cells only. Thus, reovirus enhances the accumulation of chemotherapeutic drugs only in neoplastic cells, thereby increasing both efficacy and selectivity of the chemotherapeutic agents.

In the present invention, it is preferable that reovirus increases sensitivity of cells or animals to the drug by at least about 20% as compared to the effect of the drug in the absence of reovirus. The increase in sensitivity is more preferably at least about 40%, yet more preferably at least about 70%, and even more preferably at least about 100%. In the most preferred embodiment, as in Example 1, reovirus is useful to sensitize a cell which is refractory to the drug in the absence of reovirus, and the sensitization effect cannot be numerically expressed.

The sensitivity of a cell to a drug can be observed or measured according to established methods in the art, which may vary with the nature of the disease. For example, sensitivity of a neoplastic cell to a drug may be determined by the size of the tumor or growth rate of the neoplastic cell (for instance see Example 1). Sensitivity may also be observed as reduction of the cognate symptoms or disease indicators, such as blood cell count in leukemia patients or liver function in hepatoma patients.

The present invention can be used to increase the sensitivity of neoplastic cells to any chemotherapeutic agents. Preferred chemotherapeutic agents include 5-fluorouracil, mitomycin C, methotrexate, hydroxyurea, cyclophosphamide, dacarbazine, mitoxantrone, anthracyclins (e.g., epirubicin and doxurubicin), carboplatin, cisplatin, taxol, taxotere, tamoxifen, anti-estrogens, and interferons. While new chemotherapeutic agents continue to be developed, it is expected that drug resistance to the new agents will also occur in the same manner as resistance to the known agents. Accordingly, reovirus is expected to sensitize neoplastic cells to the new chemotherapeutic agents, or to prevent neoplasia from developing drug resistance to the new agents. A skilled artisan will be able to determine if the present method applies to the new agents according to methods disclosed herein.

The reovirus is administered in a manner so that it contacts the target neoplastic cells. The route by which the reovirus is administered, as well as the formulation, carrier or vehicle, will depend on the location as well as the type of the target cells. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases, the reovirus is administered in a manner such that it can be transported systemically through the body of the mammal and thereby reach the neoplasm (e.g., intravenously or intramuscularly). Alternatively, the reovirus can be administered directly to a single solid neoplasm, where it then is carried systemically through the body to metastases. The reovirus can also be administered subcutaneously, intraperitoneally, intrathecally (e.g., for brain tumor), topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

The reovirus or chemotherapeutic agent can be administered in a single dose, or multiple doses (i.e., more than one dose). The multiple doses can be administered concurrently at different sites or by different routes, or consecutively (e.g., over a period of days or weeks). The reovirus is preferably administered prior to or concurrently with administration of the chemotherapeutic agent.

The reovirus is preferably formulated in a unit dosage form, each dosage containing from about $10^2$ pfus to about $10^{13}$ pfus of the reovirus. The term "unit dosage forms" refers to physically discrete units suitable as unitary dosages for human subjects and other mammals, each unit containing a predetermined quantity of reovirus calculated to produce the desired therapeutic effect, in association with a suitable pharmaceutical excipient.

It is contemplated that the present invention may be combined with other tumor therapies such as radiation therapy or surgery.

In addition, the present invention provides a method for preventing a neoplasm from developing drug resistance. Progressive drug resistance is developed by treating a neoplasm with a drug which kills the drug sensitive cells within the neoplasm, thereby selecting the drug resistant cells. Upon expansion of the drug resistant cells, the neoplasm manifests the phenotype of drug resistance. Accordingly, reovirus can be used to sensitize the neoplasm at the onset of the course of chemotherapy such that all cells are killed or inhibited, including the drug resistant cells. Therefore, the neoplasm so treated would have no opportunity to develop drug resistance.

A cell which is resistant to one drug is often resistant to another drug due to the phenomenon of multiple drug resistance. Therefore, reovirus is preferably administered to a neoplasm which has not been treated with any chemotherapeutic agent in order to prevent the development of drug resistance. Once drug resistance has developed, however, reovirus can still be used to sensitize the drug resistant cells and increase the efficacy and selectivity of chemotherapy, as well as directly killing the neoplastic cells by oncolysis.

As noted above, we believe that reovirus sensitizes neoplastic cells to chemotherapeutic agents by inhibiting host cell protein synthesis or inducing apoptosis. Therefore, it is contemplated that other viruses can also be used in the same manner as reovirus. In particular, the viruses that selectively infect neoplastic cells are preferred. These viruses include, but are not limited to, modified adenovirus, modified HSV, modified vaccinia virus, modified parapoxvirus orf virus, delNS1 virus, p53-expressing viruses, the ONYX-015 virus, the Delta24 virus, vesicular stomatitis virus, the herpes simplex virus 1 mutant which is defective in hrR3, Newcastle disease virus, encephalitis virus, herpes zoster virus, hepatitis virus, influenza virus, varicella virus, and measles virus. These "oncolytic" viruses are discussed below.

Adenovirus, HSV, vaccinia virus, and parapoxvirus orf virus are viruses which have developed a mechanism to overcome the double stranded RNA, kinase (PKR). Normally, when virus enters a cell, PKR is activated and blocks protein synthesis, and the virus can not replicate in this cell. However, adenovirus makes a large amount of a small RNA, VA1 RNA. VA1 RNA has extensive secondary structures and binds to PKR in competition with the double stranded RNA (dsRNA) which normally activates PKR. Since it requires a minimum length of dsRNA to activate PKR, VA1 RNA does not activate PKR. Instead, it sequesters PKR by virtue of its large amount. Consequently, protein synthesis is not blocked and adenovirus can replicate in the cell. It should be noted, however, that although the protein synthesis machinery is not blocked, host cell protein synthesis is inhibited by the virus to facilitate viral protein synthesis.

Vaccinia virus encodes two gene products, K3L and E3L, which down-regulate PKR with different mechanisms. The K3L gene product has limited homology with the N-terminal region of eIF-2α, the natural substrate of PKR, and may act as a pseudosubstrate for PKR. The E3L gene product is a dsRNA-binding protein and apparently functions by sequestering activator dsRNAs.

Similarly, herpes simplex virus (HSV) gene $_{\gamma 1}$34.5 encodes the gene product infected-cell protein 34.5 (ICP34.5) that can prevent the antiviral effects exerted by PKR. The parapoxvirus orf virus encodes the gene OV20.0L that is involved in blocking PKR activity. Thus, these viruses can successfully infect cells without being inhibited by PKR.

In the modified adenovirus, modified HSV, modified vaccinia virus, or modified parapoxvirus orf virus, the viral anti-PKR mechanism has been mutated or otherwise inactivated. Therefore, these modified viruses are not capable of replicating in normal cells which have normal PKR function. Ras-activated neoplastic cells, however, are not subject to protein synthesis inhibition by PKR, because ras inactivates PKR. These cells are therefore susceptible to infection by the modified adenovirus, modified HSV, modified vaccinia virus, or modified parapoxvirus orf virus.

The viruses can be modified or mutated according to the known structure-function relationship of the viral PKR inhibitors. For example, since the amino terminal region of E3 protein of the vaccinia virus interacts with the carboxy-terminal region domain of PKR, deletion or point mutation of this domain prevents anti-PKR function (Chang et al., 1992, 1993; 1995; Sharp et al., 1998; Romano et al., 1998). The K3L gene of vaccinia virus encodes pK3, a pseudosubstrate of PKR. There is a loss-of-function mutation within K3L. By either truncating or by placing point mutations within the C-terminal portion of K3L protein, homologous to residues 79 to 83 in eIF-2α abolish PKR inhibitory activity (Kawagishi-Kobayashi et al., 1997).

The modified HSV include, but are limited to, R3616 (both copies of the $_{\gamma 1}$34.5 gene have been deleted), R4009 (two stop codons have been inserted in the $_{\gamma 1}$34.5 gene), and G207 (mutated in the ribonucleotide reductase and the $_{\gamma 1}$34.5 genes) (Andreansky et al., 1996). These modified viruses have been used in brain tumor therapy, and it has been recently shown that R3616 preferentially infects ras-activated cells (Farassati et al., 2001).

Similarly, the delNS1 virus (Bergmann et al., 2001) is a genetically engineered influenza A virus that can selectively replicate in ras-activated neoplastic cells. The NS1 protein of influenza virus is a virulence factor that overcomes the PKR-mediated antiviral response by the host. NS1 is knocked out in the delNS1 virus, which fails to infect normal cells, presumably due to PKR-mediated inhibition, but replicates successfully in ras-activated neoplastic cells. Therefore, a modified influenza virus in which NS1 is modified or mutated, such as the delNS1 virus, is also useful in the present invention.

Other oncolytic viruses include the viruses which selectively kill neoplastic cells by carrying a tumor suppressor gene. For example, p53 is a cellular tumor suppressor which inhibits uncontrolled proliferation of normal cells. However, approximate half of all tumors have a functionally impaired p53 and proliferate in an uncontrolled manner. Therefore, a virus which expresses the wild type p53 gene can selectively kill the neoplastic cells which become neoplastic due to inactivation of the p53 gene product. Such a virus has been constructed and shown to induce apoptosis in cancer cells that express mutant p53 (Blagosklonny et al., 1996).

A similar approach involves viral inhibitors of tumor suppressors. For example, certain adenovirus, SV40 and human papilloma virus include proteins that inactivate p53, thereby allowing their own replication (Nemunaitis 1999). For adenovirus serotype 5, this protein is a 55 Kd protein encoded by the E1B region. If the E1B region encoding this 55 kd protein is deleted, as in the ONYX-015 virus (Bischoff et al, 1996; Heise et al., 2000; WO 94/18992), the 55 kd p53 inhibitor is no longer present. As a result, when ONYX-015 enters a normal cell, p53 functions to suppress cell proliferation as well as viral replication, which relies on the cellular proliferative machinery. Therefore, ONYX-015 does not replicate in normal cells. On the other hand, in neoplastic cells with disrupted p53 function, ONYX-015 can replicate and eventually cause the cell to die. Accordingly, this virus can be used to selectively infect and kill p53-deficient neoplastic cells. A person of ordinary skill in the art can also mutate and disrupt the p53 inhibitor gene in adenovirus 5 or other viruses according to established techniques.

Another example is the Delta24 virus which is a mutant adenovirus carrying a 24 base pair deletion in the E1A region (Fueyo et at., 2000). This region is responsible for binding to the cellular tumor suppressor Rb and inhibiting Rb function, thereby allowing the cellular proliferative machinery, and hence virus replication, to proceed in an uncontrolled fashion. Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell.

Yet other oncolytic viruses include the interferon sensitive viruses. Vesicular stomatitis virus (VSV) selectively kills neoplastic cells in the presence of interferon. Interferons are circulating factors which bind to cell surface receptors which ultimately lead to both an antiviral response and an induction of growth inhibitory and/or apoptotic signals in the target cells. Although interferons can theoretically be used to inhibit proliferation of tumor cells, this attempt has not been very successful because of tumor-specific mutations of members of the interferon pathway.

However, by disrupting the interferon pathway to avoid growth inhibition exerted by interferon, tumor cells may simultaneously compromise their anti-viral response. Indeed, it has been shown that VSV, an enveloped, negative-sense RNA virus rapidly replicated in and killed a variety of human tumor cell lines in the presence of interferon, while normal human primary cell cultures were apparently protected by interferon. An intratumoral injection of VSV also reduced tumor burden of nude mice bearing subcutaneous human melanoma xenografts (Stojdl et al., 2000).

Other interferon-sensitive viruses (WO 99/18799), namely viruses which do not replicate in a normal cell in the presence of interferons, can be identified by growing a culture of normal cells, contacting the culture with the virus of interest in the presence of varying concentrations of interferons, then determining the percentage of cell killing after a period of incubation. Preferably, less than 20% normal cells is killed and more preferably, less than 10% is killed.

It is also possible to take advantage of the fact that some neoplastic cells express high levels of an enzyme and construct a virus which is dependent on this enzyme. For example, ribonucleotide reductase is abundant in liver metastases but scarce in normal liver. Therefore, a herpes simplex virus 1 (HSV-1) mutant which is defective in ribonucleotide reductase expression, hrR3, was shown to replicate in colon carcinoma cells but not normal liver cells (Yoon et al., 2000).

In addition to the viruses discussed above, a variety of other viruses have been associated with tumor killing, although the underlying mechanism is not always clear. Newcastle disease virus (NDV) replicates preferentially in malignant cells, and the most commonly used strain is 73-T (Reichard et al., 1992; Zorn et al, 1994; Bar-Eli et al, 1996). Clinical antitumor activities wherein NDV reduced tumor burden after intratumor inoculation were also observed in a variety of tumors, including cervical, colorectal, pancreas, gastric, melanoma and renal cancer (WO 94/25627; Nemunaitis, 1999).

Moreover, encephalitis virus was shown to have an oncolytic effect in a mouse sarcoma tumor, but attenuation may be required to reduce its infectivity in normal cells. Tumor regression have been described in tumor patients infected with herpes roster, hepatitis virus, influenza, varicella, or measles virus (for a review, see Nemunaitis, 1999). According to the methods disclosed herein, a person of ordinary skill in the art can test the ability of these or other viruses to sensitize neoplastic cells to chemotherapeutic agents, or to prevent a neoplasm from developing drug resistance.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
hr=hour
min=minute
µM=micromolar
mM=millimolar
M=molar
ml=milliliter
µl=microliter
mg=milligram
µg=microgram
PAGE=polyacrylamide gel electrophoresis
rpm=revolutions per minute
FBS=fetal bovine serum
DTT=dithiothrietol
SDS=sodium dodecyl sulfate
PBS=phosphate buffered saline
DMEM=Dulbecco's modified Eagle's medium
α-MEM=α-modified Eagle's medium
β-ME=β-mercaptoethanol
MOI=multiplicity of infection
PFU or pfu=plaque forming units
PKR=double-stranded RNA activated protein kinase
EGF=epidermal growth factor
PDGF=platelet derived growth factor
DMSO=dimethylsulfoxide
MDR=multiple drug resistance
MRP=multidrug resistance-associated protein
HSV=herpes simplex virus

EXAMPLE 1

Sensitization of Refractory Tumor Cells to Cisplatin by Reovirus

C3H mice (Charles River) were implanted subcutaneously with $1.0 \times 10^6$ PFUs ras-transformed C3H cells (a gift of D. Edwards, University of Calgary) and allowed to develop tumors. The Dearing strain of reovirus serotype 3 used in these studies was propagated in suspension cultures of L cells and purified according to Smith (Smith et al., 1969) with the exception that β-mercaptoethanol (β-ME) was omitted from the extraction buffer. The particle/PFU ratio for purified reovirus was typically 100/1.

The tumor bearing mice were treated with 4 different regimes as described below:

| Series No. | Reovirus | Drug |
| --- | --- | --- |
| 1 | control | control |
| 2 | control | cisplatin |
| 3 | reovirus | control |
| 4 | reovirus | cisplatin |

For animals which received reovirus (Series 3-4), $5 \times 10^8$ PFUs of reovirus (in 20 µl of saline) were injected intravenously via the tail vein of the animals on Days 0, 6, 12, and 18. The animals which did not receive reovirus (Series 1-2) were injected with 20 µl of saline in the same manner and time course. Cisplatin was injected into the tail vein on Days 10, 16 and 22 at a dose of 2.5 mg per kilogram of body weight. The tumors were measured daily from Day 0 to assess growth rate of the tumors.

The tumors were refractory to cisplatin. As shown in FIG. 1, tumors treated with cisplatin alone (Series 2) progressed almost indistinguishably from the control tumors (Series 1), indicating that cisplatin had essentially no inhibitory effects on the growth rate of the tumors. In contrast, the combination of cisplatin and reovirus (Series 4) significantly reduced tumor growth. The level of inhibition by the combination was much more profound than reovirus alone (Series 3). Therefore, cisplatin contributed to tumor suppression when used in conjunction with reovirus.

We claim:

1. A method of treating a subject with a chemotherapeutic agent with a proliferative disorder, wherein said proliferative disorder comprises neoplastic cells resistant to said chemotherapeutic agent, comprising:
   (a) treating the subject with an effective amount of a reovirus under conditions that result in infection of the resistant neoplastic cells by the reovirus and that result in sensitizing the resistant neoplastic cells to the chemotherapeutic agent; and
   (b) treating the subject with an effective amount of the chemotherapeutic agent, wherein the resistant neoplastic cells are at least 20% more sensitive to the chemotherapeutic agent in the presence of the reovirus as compared to the effect of the chemotherapeutic agent in the absence of the reovirus.

2. The method of claim 1, wherein the neoplastic cells are at least 40% or 70% more sensitive to the chemotherapeutic agent as compared to the effect of the chemotherapeutic agent in the absence of reovirus.

3. The method of claim 1, wherein the reovirus is administered prior to the administration of the chemotherapeutic agent.

4. The method of claim 1, wherein the reovirus is administered concurrently with the chemotherapeutic agent.

5. The method of claim 3, wherein the reovirus is administered in multiple doses.

6. The method of claim 1, wherein the chemotherapeutic agent is cisplatin.

7. The method of claim 1, wherein the proliferative disorder is a solid tumor.

8. The method of claim 7, wherein the solid tumor is selected from the group consisting of lung cancer, prostate cancer, colorectal cancer, thyroid cancer, renal cancer, adrenal cancer, liver cancer, pancreatic-cancer, breast cancer and central and peripheral nervous system cancer.

9. The method of claim 7, wherein the virus is administered into or near the solid tumor.

10. The method of claim 1, wherein the virus is administered systemically.

11. The method of claim 1, wherein the proliferative disorder is a hematopoietic tumor.

12. The method of claim 11, wherein the hematopoietic tumor is selected from the group consisting of lymphomas and leukemias.

13. The method of claim 1, wherein the proliferative disorder is a metastatic tumor.

14. A method of sensitizing a drug resistant neoplastic cell to a chemotherapeutic agent, comprising:
   (a) contacting said drug resistant neoplastic cell resistant to the chemotherapeutic agent with an effective amount of a reovirus, said reovirus being capable of selectively infecting the drug resistant neoplastic cell; and (b) contacting said drug resistant neoplastic cell with an effective amount of the chemotherapeutic agent, the contacting of step (a) increasing the sensitivity of said drug resistant neoplastic cell to the chemotherapeutic agent by at least 20% as compared to the effect of the chemotherapeutic agent in the absence of reovirus.

15. The method of claim 14, wherein the sensitivity of the neoplastic cells is increased by at least 40% or 70% as compared to the effect of the chemotherapeutic agent in the absence of reovirus.

16. The method of claim 14, wherein the reovirus is administered prior to the administration of the chemotherapeutic agent.

17. The method of claim 14, wherein the reovirus is administered concurrently with the chemotherapeutic agent.

18. The method of claim 14, wherein the drug resistant neoplastic cell is located in a mammal.

19. The method of claim 14, wherein the chemotherapeutic agent is cisplatin.

* * * * *